# United States Patent [19]

McCanna et al.

[11] Patent Number: 6,153,568
[45] Date of Patent: Nov. 28, 2000

[54] COMPOSITIONS COMPRISING POLYQUATERNIUMS IN COMBINATION WITH POLYMERIC BIGUANIDES FOR DISINFECTING CONTACT LENSES

[76] Inventors: David J. McCanna, 211 Greystone La. Apt. 20, Rochester, N.Y. 14618; Stephen E. Maier, 47 Frazier St., Brockport, N.Y. 14420; David J. Heiler, 173 Wadsworth Ave., Avon, N.Y. 14414; Susan P. Spooner, 22 Saybrooke Dr.; Erning Xia, 93 Chippenham Dr., both of Penfield, N.Y. 14526

[21] Appl. No.: 09/190,509

[22] Filed: Nov. 12, 1998

Related U.S. Application Data

[60] Provisional application No. 60/065,510, Nov. 12, 1997.

[51] Int. Cl.[7] .......................... F61K 31/155; C11D 3/30; C11D 3/37
[52] U.S. Cl. ................... 510/112; 510/113; 510/163; 510/243; 510/384; 510/383; 510/391; 510/504; 510/475; 514/635
[58] Field of Search ............................ 510/112, 113, 510/163, 243, 384, 383, 391, 504, 475; 514/635

[56] References Cited

U.S. PATENT DOCUMENTS

| | | | |
|---|---|---|---|
| 4,443,429 | 4/1984 | Smith et al. .................. | 424/78 |
| 4,758,595 | 7/1988 | Ogunbiyi et al. ................. | 514/635 |
| 5,096,607 | 3/1992 | Mowrey-McKee et al. .......... | 252/106 |
| 5,453,435 | 9/1995 | Raheja et al. ................... | 514/402 |
| 5,543,074 | 8/1996 | Hague et al. .................... | 510/122 |
| 5,573,709 | 11/1996 | Wells ........................... | 510/122 |
| 5,661,118 | 8/1997 | Cauwet ......................... | 510/126 |
| 5,696,171 | 12/1997 | Rupp et al. ..................... | 514/700 |
| 5,711,823 | 1/1998 | Ellis et al. ...................... | 134/42 |
| 5,719,110 | 2/1998 | Cook ........................... | 510/112 |
| 5,765,579 | 6/1998 | Heiler et al. .................... | 134/42 |

FOREIGN PATENT DOCUMENTS

| | | |
|---|---|---|
| 0703996 | 6/1994 | European Pat. Off. . |
| 0776970 | 4/1997 | European Pat. Off. . |
| 1432345 | 4/1976 | United Kingdom . |
| 92/11876 | 7/1992 | WIPO . |
| 94/13774 | 6/1994 | WIPO . |
| 97/43373 | 11/1997 | WIPO . |

*Primary Examiner*—Kery Fries

[57] ABSTRACT

The present invention is directed to an ophthalmically safe disinfecting solution for contact lenses comprising the combination of a polymeric biguanide and a polyquaternium polymer of a substituted or unsubstituted vinylimidazole or its vinylimidazoliuum salt, which copolymer has a weight average molecular weight of 5,000 to 5,000,000. The invention is also directed to an improved method of disinfecting a contact lens.

23 Claims, No Drawings

COMPOSITIONS COMPRISING POLYQUATERNIUMS IN COMBINATION WITH POLYMERIC BIGUANIDES FOR DISINFECTING CONTACT LENSES

This application claims the benefit of U.S. Provisional Application No(s).: 60/065,501 filed on Nov. 12, 1997.

FIELD OF THE INVENTION

This invention relates to new and improved solutions for the treatment of contact lenses and to methods for treating contact lenses with such solutions. In particular, the present invention is directed to disinfecting solutions comprising the combination of a biguanide polymer and a polyquaternium copolymer of substituted or unsubstituted vinylimidazole or its vinylimidazoliuum salt.

BACKGROUND OF THE INVENTION

Generally, contact lenses in wide use fall into three categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, and (3) gel, hydrogel or soft type lenses made of polymerized hydrophilic or hydrophobic monomers, such as 2-hydroxyethyl methacrylate (HEMA). The hard acrylic type contact lenses are characterized by low water vapor diffusion constants, resistance to the effects of light, oxygen and hydrolysis, and absorb only minor amounts of aqueous fluids. Because of the durability of hard contact lenses, coupled with their tendency not to absorb appreciable amounts of water, the selection of suitable disinfecting agents, cleaning agents or other lens care compounds is relatively non-critical.

However, unlike hard lenses, soft-type contact lenses have a tendency to bind and concentrate significantly more fluids, environmental pollutants, water impurities, as well as antimicrobial agents and other active ingredients commonly found in lens-care solutions. In most instances, the low levels of the ingredients in lens-care solutions do not lead to eye tissue irritation when used properly. Nevertheless, especially due to the inherent binding action of protein deposits to soft-lens materials, some disinfecting agents and preservatives tend to build up on lens surfaces and may become concentrated to potentially hazardous levels, such that when released could cause corneal inflammation and other eye tissue irritation.

Certain antibacterial agents were found to be more compatible with contact lenses and exhibit less binding on lens surfaces. In one case, it was found that chlorhexidine, a biguanide, binds to soft lens material seven times less than benzalkonium chloride. The presence of proteinaceous oily tear-film deposits on a lens, however, can double the amount of chlorhexidine absorbed on the lens compared to a clean lens. U.S. Pat. No. 4,354,952 discloses very dilute disinfecting and cleaning solutions containing chlorhexidine or its salt in combination with certain amphoteric and non-ionic surfactants. These solutions were found to reduce the amount of binding of chlorhexidine on hydrophilic soft contact lenses. Notwithstanding the reduction in binding achieved by this invention, the use of chlorhexidine did result in certain tradeoffs. The antimicrobial activity of the chlorhexidine may be diminished when used with certain amphoteric surfactants. Furthermore, it was reported that if not used in proper ratio, the surfactant and disinfectant will precipitate unless a non-ionic type surfactant is also employed.

The use of certain ionic polymers in contact-lens cleaning and preserving solutions is also known. For example, U.S. Pat. No. 5,096,607 and WO 94/13774 disclose the use of certain polyquaterniums as antimicrobial agents, typically in amounts less than 100 parts-per-million (ppm) in actual commercial practice. U.S. Pat. No. 4,443,429 to Smith et al. discloses the use in a contact-lens disinfecting solution of a dimethyldiallyammonium chloride homopolymer known as Merquat® 100 having a molecular weight of about 10,000 to about 1,000,000. Polyquaternium polymers in general are a well known class of polymers, many variations of which are commercially available. The CTFA International Cosmetic Ingredient Dictionary includes polyquaterniums designated Polyquaternium-1 through Polyquaternium 44, and new polyquaterniums are in continuous development.

British Patent 1,432,345 discloses contact lens disinfecting compositions containing a polymeric biguanide and a mixed phosphate buffer. Compositions as disclosed by this patent, however, have corneal staining values of 17% or more, far above that which is desirable for patient acceptability.

U.S. Pat. No. 4,758,595 to Ogunbiyi et al. disclosed that a contact-lens solution containing a polyaminopropyl biguanide (PAPB), also known as polyhexamethylene biguanide (PHMB), has enhanced efficacy when combined with a borate buffer. These disinfecting and preservative solutions are especially noteworthy for their broad spectrum of bactericidal and fungicidal activity at low concentrations coupled with very low toxicity when used with soft-type contact lenses.

U.S. Pat. No. 5,453,435 to Raheja et al., disclosed a preservative system that comprises a combination of chlorhexidine and polyhexamethylene biguanide. This preservative system, used in commercial products for rigid-gas-permeable lenses, was found to exhibit an improved combination of efficacy and low eye irritation.

Compositions containing PHMB and borate have been commercialized in various products, but at levels of about 1 ppm or less for use with soft contact lenses. It is generally desirable to provide the lowest level of a bactericide possible, while maintaining the desirable level of disinfection efficacy, in order to provide a generous margin for safety and comfort.

Some of the most popular products for disinfecting lenses are multipurpose solutions that can be used to clean, disinfect and wet contact lenses, followed by direct insertion (placement on the eye) without rinsing. Obviously, the ability to use a single solution for contact-lens care is an advantage. Such a solution, however, must be particularly gentle to the eye, since, as indicated above, some of the solution will be on the lens when inserted and will come into contact with the eye.

With conventional contact-lens cleaners or disinfectants, including multi-purpose solutions, lens wearers typically need to digitally or manually rub the contact lenses (typically between a finger and palm or between fingers) during treatment of the contact lenses. The necessity for the daily "rubbing" of contact lenses adds to the time and effort involved in the daily care of contact lenses. Many contact-lens wearers dislike having to perform such a regimen or consider it to be an inconvenience. Some wearers may be negligent in the proper "rubbing" regimen, which may result in contact-lens discomfort and other problems. Sometimes rubbing, if performed too rigorously, which is particularly apt to occur with beginning lens wearers, may damage the lenses. This can be problematic when a replacement lens is not immediately available.

Contact lens solutions that qualify as a "Chemical Disinfecting Solution" do not require rubbing to meet biocidal performance criteria (for destroying representative bacteria and fungi) set by the US Food and Drug Administration (FDA) under the Premarket Notification (510k) Guidance Document For Contact Lens Care Products, May 1, 1997. In contrast, a contact-lens solution, referred to as a "Chemical Disinfecting System," that does not qualify as a Chemical Disinfecting Solution, requires a rubbing regimen to pass biocidal performance criteria. Traditionally, multi-purpose solutions (used for disinfecting and wetting or for disinfecting, cleaning, and wetting) have qualified as a Chemical Disinfecting System, but not as a Chemical Disinfecting Solution.

A Chemical Disinfecting Solution would generally require a more efficacious or stronger disinfectant than a Chemical Disinfecting System. The stronger the biocidal effect of a solution, however, the more likely that it may exhibit toxic effects or adversely effect lens-wearer comfort. For example, many very efficacious bactericides used in other contexts, such as mouthwashes, cosmetics, or shampoos, while being sufficiently safe for use in such products, would be too toxic for ophthalmic use, especially for use with soft lenses because of the above-mentioned tendency of soft lenses to bind chemicals and the sensitivity of eye tissues. Similarly, the concentrations of certain bactericides may need to be within lower limits in solutions for use with soft contact lenses than in other products or in solutions for other types of lenses, especially when such solutions are not rinsed from the contact lens before placing the lens in the eye.

It would be desirable to obtain a contact-lens solution that would simultaneously provide both (1) an increased level and/or broader spectrum of biocidal activity, and (2) a low order of toxicity to eye tissue, such that the solution can be used to treat a contact lens such that the lens can subsequently be placed on the eye without rinsing the solution from the lens. While challenging to develop, it would be especially desirable to obtain a Chemical Disinfecting Solution that could be used for soft contact lenses and that would allow direct placement of a contact lens on an eye following soaking in the solution and/or rinsing and rewetting with the solution. Such a product may provide increased efficacy, resulting in greater protection to the lens wearer against infection caused by microorganisms, while providing maximum convenience. Finally, it would be desirable for the biocidal efficacy of the disinfecting solution to be sufficiently high to achieve efficacious disinfection, or at least not inherently inefficacious disinfection, of a contact lens with respect to bacteria and fungi in the event, for whatever reason, that the contact lens wearer does not carry out a regimen involving mechanical rubbing or the like using the contact-lens solution.

BRIEF DESCRIPTION OF THE INVENTION

The present invention is directed to an ophthalmically safe disinfecting solution for contact lenses comprising:

(a) between about 0.10 and about 3.0 ppm (between 0.00001 and 0.0003 percent by weight) of a polymeric biguanide, or water-soluble salt thereof, having the following formula:

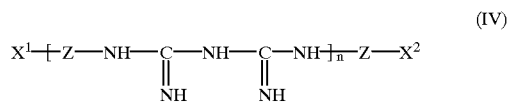

wherein Z is an organic divalent bridging group which may be the same or different throughout the polymer, n is 1 to 500, and $X^1$ and $X^2$ are independently selected from the groups —$NH_2$ and

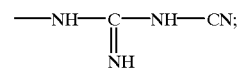

and b) between about 10 to about 400 ppm of active ingredient (between 0.0010 and 0.04 percent by weight) of at least one polyquaternium comprising 10 to 45 mole percent of repeat units derived from substituted or unsubstituted vinylimidazoles or their vinylimidazoliuum salts which copolymer has a weight average molecular weight of 5,000 to 5,000,000.

DETAILED DESCRIPTION OF THE INVENTION

The combined used of the biguanide polymer and polyquaternium polymer described herein offers greater convenience and/or protection for lens wearers against microorganisms compared to traditional disinfecting products for contact lenses. This combination of disinfecting agents provides a broader, more potent and faster antimicrobial activity across the entire range of microorganisms, as evidenced by representative bacteria and fungi commonly tested. Biguanide polymers such as PHMB have been shown to be effective biocidal agents. PHMB, however, is less effective against fungi than bacteria. The class of polyquaternium polymers described herein, on the other hand, has been found by the Applicants to be relatively effective against fungi and less effective against bacteria so that the biocidal spectrum of the polyquaternium described herein has been found to advantageously and unexpectedly complement the biocidal spectrum of biguanide polymers such as PHMB.

In particular, solutions according to the present invention provide a broader, more potent and faster antimicrobial activity overall, when considering the entire range of microorganisms, based on representative bacteria and fungi commonly tested. In particular, the disinfecting solutions of the present invention are effective at low concentrations against a wide spectrum of microorganisms, including but not limited to *Staphylococcus aureus, Pseudomonas aeruginosa, Serratia marcescens, Candida albicans*, and *Fusarium solani*.

A disinfecting solution is generally defined as a contact-lens care product containing one or more active ingredients (for example, anti-microbial agents and/or preservatives) in sufficient concentrations to destroy harmful microorganisms on the surface of a contact lens within the recommended minimum soaking time. The recommended minimum soaking time is included in the instructions for use of the disinfecting solution. The term "disinfecting solution" does not exclude the possibility that the solution may also be useful as a preserving solution, or that the disinfecting solution may also be useful for other purposes such as daily cleaning, rinsing and storage of contact lenses, depending on the particular formulation. The present solution, in combination with its container or bottle and packaging, including instructions for use in accordance with a specified regimen, may be considered a novel and improved kit, package, or system for the care of contact lenses.

By the term "soft lens" is meant a lens having a proportion of hydrophilic repeat units such that the water content of the lens during use is at least 20% by weight. The term "soft contact lens" as used herein generally refers to those contact lenses which readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. However, newer soft lenses are being made from high-Dk silicone-containing materials.

By the term "ophthalmically safe" with respect to a contact-lens solution is meant that a contact lens treated with the solution is safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO standards and U.S. FDA (Food & Drug Administration) regulations.

A solution that is useful for cleaning, chemical disinfection, storing, and rinsing a soft contact lens is referred to herein as a "multi-purpose solution." Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more cleaning agents in sufficient concentrations to loosen and remove loosely held lens deposits and other contaminants on the surface of a contact lens, especially if used in conjunction with digital manipulation (for example, manual rubbing of the lens with a solution) or with an accessory device that agitates the solution in contact with the lens, for example, a mechanical cleaning aid. The critical micelle concentration of a surfactant-containing solution is one way to evaluate its cleaning effectiveness.

The term "effective multi-purpose solution" analogously refers to a solution useful for daily chemical disinfection, storing, and rinsing a contact lens, which solution does not claim to clean a contact lens, but which solution still obviates the need for any other solution for daily cleaning, that is, no other solution must necessarily be used in conjunction or combination with the solution on a daily basis. Although such solutions may comprise a surfactant or other agent that may inherently loosen or preventing lens deposits to some extent, such solutions are not necessarily capable of cleaning a contact lens. Effective multi-purpose solutions are therefore only applicable for lenses used for limited period of time, either disposable or frequent replacement lenses.

Traditionally, multi-purpose solutions on the market require a regimen involving mechanical rubbing of the contact lens with the multi-purpose solution, in order to provide the required disinfection. That is, such a regimen is required under governmental regulatory authorities (for example, the FDA or Food & Drug Administration in the USA) for a Chemical Disinfection System that does not qualify as a Chemical Disinfecting Solution. The invention according to the present invention has the advantage that it is possible to formulate a product that, on the one hand, is gentle enough to be used as both a disinfecting solution and a wetting agent and, on the other hand, is able to meet the biocidal performance disinfection for a Chemical Disinfecting Solution under criteria established by the US FDA for Contact Lens Care Products (May 1, 1997) that does not require a regimen involving rubbing of the lenses (even though rubbing of the lens may provide further removal of microorganisms). In other words, the compositions according to the present invention may optionally be formulated to meet the requirements of the FDA or ISO Stand-Alone Procedure for contact lens disinfecting products. Accordingly, it is possible to make formulations that offer higher patient compliance and greater universal appeal than traditional disinfecting or disinfecting and cleaning products.

It is noted that the combination of the biguanide polymer and the polyquaternium according to the present invention provides enhanced efficacy while not causing irritation or discomfort to the eyes, always an important and challenging concern in the art of contact-lens care. Thus, increased amounts of the biguanide polymer, by itself, to achieve the same efficacy as the combination would result in greater eye irritation. Specifically, it has been found that increased amounts of the biguanide polymer, by itself, to achieve the necessary disinfection for a Chemical Disinfecting Solution would result in unacceptable eye irritation. Even if a rubbing regimen is recommended when using solutions of the present invention, the enhanced biocidal activity may provide greater protection against infection, especially if the rubbing by the contact-lens wearer is inadequate or omitted through negligence or disregard of the product instructions.

As indicated above, the combination of a biguanide polymer and a polyquaternium polymer has been found to result in strong anti-microbial activity across the entire range of microorganisms typically associated with ophthalmic preservation and disinfection. Other advantages of the present disinfecting system have been found. The polyquaternium polymer used in the present invention has been found to inhibit protein deposition on hydrophilic contact lenses, and the polymer has been found to stabilize the biguanide polymer known as PHMB over the shelf life of the product.

The polyquaternium polymer employed in the present invention comprise 10 to 45 mole percent of a quaternary-amine-functional repeat unit that is the copolymerization reaction product of one or more comonomers selected from the group consisting of substituted or unsubstituted vinylimidazoles or their vinylimidazolium salts and mixtures thereof. By the term "quaternary-amine-functional repeat unit" is herein meant that the repeat unit comprises a quaternary-amine group in which a positively charged nitrogen atom is covalently bonded to four radicals (no hydrogen atoms) and ionically bonded to a negatively charged counterion such as chloride.

The polyquaternium polymers of the present invention suitably have a weight average molecular weight $M_w$ of about 5,000 to 5,000,000, preferably about 10,000 to 500,000, most preferably about 20,000 to 200,000.

The polyquaternium polymers useful in the present invention may include, but is not limited to, copolymers in which the quaternary-amine-functional repeat units are derived from 1-vinyl and 3-methyl-1-vinylimidazole, 1-vinyl- and 3-methyl-1-vinylimidazolium, their halides or other salt forms, derivatives thereof, and mixtures of the above. Preferably, the polyquaternium polymer comprises 10 to 45 mole percent of repeat units derived from a vinylimazole or vinylimidazolium comonomer and 90 to 55 mole percent of repeat units derived from one or more neutral comonomers such as vinylpyrrolidone. The polyquaternium polymer suitably includes an opthalmologically suitable anionic organic or inorganic counterion. A preferred counterion is chloride.

Up to 90%, preferably 40% to 90% by mole, of copolymerization-compatible comonomers not having a quaternary-amine-functionality may be copolymerized with the quaternary-amine-functional comonomers. Suitable comonomers include, but are not limited to, vinylpyrrolidone, acrylamide, acrylic acid, alkyl methacryate, tertiary amines such as N,N-dialkylaminoalkyl acrylate and methacrylate, and copolymerization-compatible mixtures thereof. A preferred alkyl group has 1 to 6 carbon atoms. Most preferably, alkyl groups are methyl, ethyl, and/or butyl.

Up to 25% by mole, preferably 0% to 10% by mole, of copolymerization-compatible comonomers having a quaternary-amine-functionality, other than those quaternary-amine-functional monomers described above, may be copolymerized. Examples include the dimethyldiallyl salt.

The polymerization techniques for the preparation of the polyquaterniums used in the present invention are well known to those skilled in the art and many variations of such techniques are similarly in practice in commerce. New variations of polyquaternium polymers meeting the present invention are in continuous commercial development, for example, various polymers having different combinations of the same or similar repeat units, different relative proportions of comonomers, and/or different molecular weights are in continuous commercial development.

A particularly preferred polyquaternium copolymer is Luviquat® 370 polymer (CTFA International Cosmetic Ingredient Dictionary designation polyquaternium-16, commercially available from BASF, Ludwigshafen, Germany) which is the polymerization product of a mixture of comonomers of which 70% is vinylpyrrolidone and 30% is vinylimidazolium methochloride, commercially available as a composition with a solids content of about 40% by weight in water.

In the present composition, the polyquaternium copolymer is suitably present in an amount less than 400 ppm of active ingredient, between about 10 and 400 ppm (between 0.001 and 0.04 percent by weight of the composition), preferably between 25 and 300 ppm (between 0.0025 and 0.03 percent by weight) in aqueous solution, more preferably between about 50 ppm and about 200 ppm (between 0.005 and 0.02 percent by weight), most preferably about 100 ppm (0.01 percent by weight). In one particular embodiment of the invention, the amount of the copolymer is less than 100 ppm, between about 10 and 100 ppm or from 10 to 99 ppm (0.001 to 0.0099 weight percent). All ppms of the copolymer used herein are with respect to the amount of active ingredient, and the amounts of commercially available aqueous solutions of a copolymer that are used in making solutions according to the present invention must be adjusted accordingly. The contact-lens solution comprises 80 to 99% by weight, preferably 93 to 99% by weight, water.

The second component of the preservative/disinfecting system of the present invention is a polymeric biguanide (one or more), and water-soluble salts thereof, having the following formula:

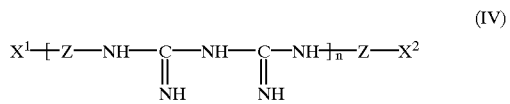

wherein Z is an organic divalent bridging group which may be the same or different throughout the polymer, n is on average at least 3, preferably 5 to 20, and $X^1$ and $X^2$ are independently selected from the groups —$NH_2$ and

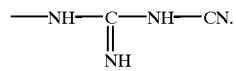

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

The polymeric biguanides, in combination with the polyquaternium of the present invention, are effective in concentrations as low as 0.00001 weight percent (0.1 ppm). The total concentration of a polymeric biguanide of Formula (IV) or (V) (irrespective of the particular salt form or whether the free base is used ) may in total be as low as about 0.000010 weight percent (0.10 ppm) and up to about 0.00030 weight percent (3.0 ppm) in the present invention, whether in the form of a water-soluble salt or the free base.

Most preferred are the polymeric hexamethylene biguanides (commercially available as the hydrochloride salt from Zeneca, Wilmington, Del., under the trademark Cosmocil™ CQ). Such polymers and their water-soluble salts are also referred to as polyaminopropyl biguanide (PAPB). The term polyhexamtheylene biguanide (PHMB), as used herein, is meant to encompass one or more biguanides have the following formula:

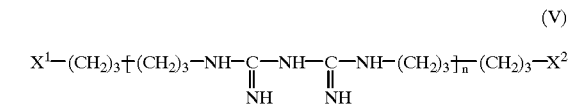

wherein $X^1$ and $x^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated herein by reference. Preferably, the water-soluble salts are compounds where n has an average value of 2 to 15, most preferably 3 to 12.

The disinfecting solutions used with this invention may optionally contain other antimicrobial agents which are compatible. As used herein, antimicrobial agents are defined as non-oxidative organic chemicals which derive their antimicrobial activity through a chemical or physiochemical interaction with the microbial organisms. Suitable antimicrobial agents are polymeric quaternary ammonium salts used in ophthalmic applications such as poly [(dimethyliminio)-2-butene-1,4-diyl chloride], [4-tris(2-hydroxyethyl) ammonio]-2-butenyl-w-[tris(2-hydroxyethyl) ammonio]dichloride (chemical registry number 75345-27-6) generally available as polyquaternium 1 ® from ONYX Corporation, benzalkonium halides, and bis(biguanides) such as salts of alexidine, alexidine free base, and salts of chlorhexidine. The antimicrobial agents used herein are preferably employed in the absence of mercury-containing compounds such as thimerosal. The salts of alexidine and chlorhexidine can be either organic or inorganic and are typically gluconates, nitrates, acetates, phosphates, sulphates, halides and the like. Typically, such agents may be used in concentrations of 0.00001% (w/v) or higher.

The solutions of the present invention may be formulated into specific contact lens care products, such as wetting solutions, soaking solutions, cleaning and conditioning solutions, as well as purpose type lens care solutions, etc. and mixtures thereof.

When used in a cleaner, neutral (non-ionic) surfactants may impart additional cleaning and conditioning properties and are usually present in amounts up to 15 weight percent. Suitable surfactants can be either amphoteric, cationic, anionic, or nonionic which may be present (individually or in combination) in amounts up to 15 percent, preferably up to 5 percent by weight of the composition or solution. Preferred surfactants are amphoteric or nonionic surfactants, which when used impart cleaning and conditioning properties. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determined the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available under the trademark Tween® 20), polyoxyethylene (23) lauryl ether (Brij® 35), polyoxyethyene (40) stearate (Myrj® 52), polyoxyethylene (25) propylene glycol stearate (Atlas® G 2612). One non-ionic surfactant in particular consisting of a poly(oxypropylene)-poly (oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under the registered trademark "Tetronic". An analogous of series of surfactants, suitable for use in the present invention, is the poloxamer series which is a poly(oxyethylene) poly(oxypropylene) block polymers available under the trademark "Pluronic" (commercially available form BASF).

Various other ionic as well as amphoteric and anionic surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and *the CTFA International Cosmetic Ingredient Handbook*, Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants when employed with a buffer enhancer will generally be present in an amount from 0.01 to 5.0 percent (w/w), preferably 0.1 to 5.0 percent.

Typically, the aqueous solutions of the present invention for treating contact lenses are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

The pH of the present solutions should be maintained within the range of 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred, particularly for enhancing the efficacy of biguanides. Generally, buffers will be used in amounts ranging from about 0.05 to 2.5 percent by weight, and preferably, from 0.1 to 1.5 percent. The disinfecting/preserving solutions of this invention preferably contain a borate buffer system, containing one or more of boric acid, sodium borate, potassium tetraborate, potassium metaborate or mixtures of the same. In addition to buffering agents, in some instances it may be desirable to include sequestering agents in the present solutions in order to bind metal ions which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent. Other suitable sequestering agents include gluconic acid, citric acid, tartaric acid and their salts, e.g. sodium salts. Still other more powerful sequestering agents can be used to further inhibit the deposition of proteins on the lenses, for example, the phosphonates disclosed in WO 97/31659.

The solutions of the present invention may be formulated into specific contact lens care products, such as wetting solutions, soaking solutions, cleaning and conditioning solutions, as well as multi-purpose type lens care solutions, etc. and mixtures thereof. Such solutions may also be formulated for application to a contact lens while it is still in the eye, for example, in the form of droplets.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose, povidone, polyvinyl alcohol, and the like. Such viscosity builders may be employed in amounts ranging from about 0.01 to about 4.0 weight percent or less. The present solutions may also include optional demulcents.

The aqueous solutions according to the present invention can be effectively used in disinfecting contact lenses by any of the well recognized methods. The lenses may be treated by the "cold" soaking method at room temperature for a period ranging from about 5 minutes to about 12 hours. The lenses are then removed from the solution, rinsed with the same or a different solution, for example a preserved isotonic saline solution and then replaced on the eye.

As indicated above, contact-lens wearers are commonly required to digitally or manually rub the contact lenses (typically between a finger and palm or between fingers) during daily cleaning and/or disinfecting of contact lenses. In one embodiment of the present invention, a method is provided in which rubbing is not required during treatment with the claimed specified solution, between removal from the eye and replacement of the lens following lens care. In a preferred embodiment of such a method, a soft lens is disinfected or both disinfected and cleaned with a multipurpose solution or an effective multipurpose solution that is the only daily solution needed for treating the lens outside the eye. Thus, in one embodiment of a method according to the invention, the described solution is used to treat a contact lens without rubbing, by a method comprising:

(a) soaking the contact lens that has not been rubbed with the solution for a specified time period, and (b) direct placement of the treated contact lens on the eye of the wearer.

Typically, step (a) may involve immersing the contact lens in the solution. Soaking may optionally comprise shaking or similarly agitating a container of the solution by manual means. Preferably, step (a) involves a period of soaking the contact lens in a container wherein the contact lens is completely immersed in the solution. By the term "direct placement" is herein meant that the solution is not diluted or rinsed off the lens with a different contact-lens solution prior to "insertion" or placement on the eye. In a particularly preferred embodiment, the method uses a no-rub multi-purpose or effective multi-purpose solution, wherein no other solution or product is required for daily cleaning of the lens, with the possible exception of an enzyme cleaner.

In yet another embodiment of a method according to the present invention, the claimed solution is used to clean a soft lens that is a frequent replacement lens (FRL), planned for replacement after not more than about three months of use in the eye, or that is planned for replacement after not more than about 30 days of use in the eye, or that is planned for replacement after not more than about two weeks in the eye. Preferably, the lens is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate.

The following Examples illustrate the compositions and methods of the instant invention.

EXAMPLE 1

This example illustrates one embodiment of the present composition for treating contact lens. The components of the composition are as follows:

TABLE 1

| Ingredient | mg/gm | % w/w |
|---|---|---|
| Polyhexamethylene Biguanide HCL (as Cosmocil ® CQ) (20% w/w solution PHMB) | 0.0047 | 0.00047 |
| Boric Acid | 6.6 | 0.66 |
| Sodium Borate | 1.0 | 0.1 |
| Edetate Disodium | 1.0 | 0.1 |
| Sodium Chloride | 5.4 | 0.54 |
| Poloxamine** 1107 | 10.0 | 1.0 |
| Luviquat ® FC370* polymer (in 40% w/w solution)) | 0.10 | 0.010 |
| Hydrochloric Acid, 1N | adjust to pH 7.1–7.4 | |
| Sodium Hydroxide, 1N | adjust to pH 7.1–7.4 | |
| Purified Water, qs to | 1.00 gm | 100% |

*a trademark of BASF, Ludwigshafen, Germany.
**molecular weight 14,500, Tetronic ® 1107, a poly(oxypropylene) poly (oxyethylene) block copolymer adduct of ethylene diamine, a trademark of BASF Wyandotte Corp., Wyandoffe, MI.

To a stainless steel vessel is added purified water to approximately 85% of total batch weight. The vessel is then placed on a hot plate equipped with a mixer, and the solution is warmed to approximately 60° C. with mixing. The buffer and other salts are added one at a time, making sure that each is dissolved before adding the next salt. The heat is then turned off and Poloxamine 1107 is added with constant mixing. The Luviquat® FC 370 polymer is added and mixed to dissolve. The solution, after optional autoclaving, is allowed to cool and PHMB solution is added through a sterile filter and qs to the desired weight with water. The pH and osmolality of the formulation is measured and adjusted to a pH of 7.2+/−0.1 if necessary.

EXAMPLE 2

This Example illustrates the preparation of an aqueous contact-lens disinfectant solution according to the present invention.

TABLE 2

| | Percent (w/w) |
|---|---|
| Luviquat* FC 370 polyquaternium polymer (in 40% solution) | 0.010 |
| PHMB biguanide polymer (in 20% solution) | 0.00008 |
| Poloxamine 1107 ** | 1.000 |
| Dequest*** 2016 phosphonate | 0.100 |
| Sodium Carbonate | 0.100 |
| Boric Acid | 0.830 |
| Sodium Phosphate (Dibasic Anhydrous) | 0.310 |
| Sodium Phosphate (Monobasic, Anhydrous) | 0.10 0.150 |
| Sodium Chloride | 0.330 |
| Distilled Water qs | 100.0 |

*a trademark of BASF, Ludwigshafen, Germany.
**molecular weight 14,500, Tetronic ® 1107, a poly(oxypropylene) poly (oxyethylene) block copolymer adduct of ethylene diamine, a trademark of BASF Wyandotte Corp., Wyandotte, MI.
***a trademark of Monsanto Co., St. Louis, MI.

To a stainless steel vessel is added purified water to approximately 85% of total batch weight. The vessel is then placed on a hot plate equipped with a mixer, and the solution is warmed to approximately 60° C. with mixing. The buffer and other salts are added one at a time, making sure that each is dissolved before adding the next salt. The heat is then turned off and Poloxamine 1107 is added with constant mixing. The Luviquat® FC 370 polymer is added and mixed to dissolve. The solution, after optional autoclaving, is allowed to cool and PHMB solution is added through a sterile filter and qs to the desired weight with water. The pH and osmolality of the formulation is measured and adjusted to a pH of 7.2+/−0.1 if necessary.

COMPARATIVE EXAMPLE 3

This Comparative Example illustrates the preparation of an aqueous contact-lens disinfectants solution without the polyquaternium polymer.

TABLE 3

|  | Percent (w/w) |
| --- | --- |
| PHMB biguanide polymer (in 20% solution) | 0.00008 |
| Poloxamine 1107* | 1.000 |
| Na$_2$EDTA | 0.110 |
| Boric Acid | 0.660 |
| Sodium Borate | 0.100 |
| Sodium Chloride | 0.54 |
| Hydrochloric Acid | as needed |
| Sodium Hydroxide | as needed |
| Distilled Water qs | 100.0 |

*molecular weight 14,500, Tetronic® 1107, a poly(oxypropylene) poly (oxyethylene) block copolymer adduct of ethylene diamine, a trademark of BASF Wyandotte Corp., Wyandotte, MI.

The solution can be prepared by gradually heating 80 percent of the water to 80° C. while dissolving the disodium EDTA therein. The boric acid and sodium borate buffers are added to the heated solution of disodium EDTA and dissolved. The sodium chloride is then added to the solution and dissolved, followed by the addition of the poloxamine surfactant. Hydrochloric acid and sodium hydroxide are added as needed to obtain a pH of 7.2. The osmolality is 280–320 mOSm/kg. The solution is sterilized by autoclaving to 120° C. for 45 minute. After the solution is cooled to room temperature, the biguanide polymer is added through a sterile filter, followed by the balance of distilled water.

EXAMPLE 4

This Example illustrates the microbicidal efficacy of a solution according to the present invention. The antimicrobial efficacy was evaluated as follows. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231), and *Fusarium solani* (ATCC 36031). The test organisms were cultured on appropriate agar and the cultures were harvested using sterile DPBST (Dulbecco's Phosphate Buffered Saline plus 0.05% w/v polysorbate 80) or a suitable diluent and transferred to a suitable vessel. Spore suspensions were filtered through sterile glass wool to remove hyphal fragments. *Serratia marcescens*, as appropriate, was filtered (eg., through a 1.2µfilter) to clarify the suspension. After harvesting, the suspension was centrifuged at no more than 5000×g for a maximum of 30 minutes at 20–25° C. The supernatant was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1\times10^7$–$10^8$ cfu/mL. The appropriate cell concentration may be estimated by measuring the turbidity of the suspension, for example using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1.0\times10^5$–$10^6$ cfu/mL, the volume of the inoculum not exceeding 1% of the sample volume. Dispersion of the inoculum was ensured by vortexing the sample for at least 15 seconds. The inoculated product was stored at 10–25° C. Aliquots in the amount of 1.0 mL were taken of the inoculated product for determination of viable counts after certain time periods of disinfection. The time points for the bacteria were, for example, 1, 2, 3, and 4 hours when the proposed regimen soaking time was 4 hours. Yeast and mold were tested at an additional time point of $\geq 16$ hours (4 times the regimen time). The suspension was mixed well by vortexing vigorously for at least 5 second. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of trypticase soy (TSA) agar for bacteria and Sabouraud dextrose agar (SDA) for mold and yeast. The bacterial recovery plates were incubated at 30–35° C. for 2–4 days. The yeast was incubated at 20–30° C. for 2–4 days and mold recovery plates at 20–25° C. for 3–7 day average number of colony forming units was determined on countable plates. Countable plates refer to 30–300 cfu/plates for bacteria and yeast, and 8 to 80 cfu/plate for mold except when colonies are observed only for the $10^0$ or $10^{-1}$ dilution plates. The microbial reduction was then calculated at the specified time points. In order to demonstrate the suitability of the medium used for growth of the test organisms and to provide an estimation of the initial inoculum concentration, inoculum controls were made by dispersing an identical aliquot of the inoculum into a suitable diluent, for example DPBST, using the same volume of diluent used to suspend the organism as listed above. Following inoculation in a validated neutralizing broth and incubation for an appropriate period of time, the inoculum control must be between $1.0\times10^5$–$1.0\times10^6$ cfu/mL The solutions were evaluated based on the performance requirement referred to as the "Stand-Alone Procedure for Disinfecting Products" (hereafter the "stand-alone test") and is based on the Disinfection Efficacy Testing for contact lens care products under the Premarket Notification (510(k)) Guidance Document For Contact Lens Care Products dated May 1, 1997, prepared by the U.S. Food and Drug Administration, Division of Ophthalmic Devices. This performance requirement is comparable to current ISO standards for disinfection of contact lenses (revised 1995). The stand-alone test challenges a disinfecting product with a standard inoculum of a representative range of microorganisms and establishes the extent of viability loss at pre-determined time intervals comparable with those during which the product may be used. There is a primary performance criteria and secondary performance criteria. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time.

This Example shows the comparable antimicrobial efficacy of the solution of Example 2 above compared to the comparative solution of Comparative Example 3 above using the testing procedures described above, at time intervals of 1 hour, 2 hours, 3 hours, and 4 hours for bacteria, and at 1 hour, 2 hours, 3 hours, 4 hours, and 24 hours for the fungi (yeast and mold). The results are shown in Table 4 below.

TABLE 4

| Microorganism Tested | Time Tested | Biguanide and Polyquaternium (Ex 2) | Biguanide Polymer Alone (Comparative Ex 3) |
|---|---|---|---|
| Staphylococcus aureus | 1 hr | 4.5 | 3.5 |
| | 2 hr | >4.8 | >4.8 |
| | 3 hr | >4.8 | >4.8 |
| | 4 hr | >4.8 | >4.8 |
| Pseudomonas aeruginosa | 1 hr | >4.7 | 4.5 |
| | 2 hr | >4.7 | >4.7 |
| | 3 hr | >4.7 | >4.7 |
| | 4 hr | >4.7 | >4.7 |
| Serratia marcescens | 1 hr | 3.9 | 4.2 |
| | 2 hr | >4.6 | >4.6 |
| | 3 hr | >4.6 | >4.6 |
| | 4 hr | >4.6 | >4.6 |
| Candida albicans | 1 hr | 2.5 | 2.5 |
| | 2 hr | 3.3 | 2.9 |
| | 3 hr | 4.0 | 3.2 |
| | 4 hr | 3.9 | 3.1 |
| | 24 hr | >4.7 | 3.1 |
| Fusarium solani | 1 hr | 2.1 | 0.8 |
| | 2 hr | 2.3 | 0.9 |
| | 3 hr | 2.8 | 1.1 |
| | 4 hr | 3.3 | 1.1 |
| | 24 hr | >4.4 | 2.9 |

The results from the ISO/CEN Stand-Alone testing indicate that the presence of polyquaternium-16 enhanced the biocidal efficacy of the formulation against *Candida albicans* and *Fusarium solani*. Moreover, the composition according to the present invention (biguanide polymer and polyquaternium) is able to meet the ISO Stand-Alone Procedure for Contact Lens Disinfecting Products requirements at 4 hours. In comparison, the comparative example (biguanide polymer alone) did not pass the stand-alone test at 1 hour and 2 hours and only just passed the test at 3 hours and 4 hours, indicating that the product would not dependably disinfect a contact lens against the standard test bacteria and fungi without a rubbing regimen, especially in view of the fact that the amount of biguanide polymer in a product may decrease somewhat over its shelf-life.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

We claim:

1. An ophthalmically safe solution for treating contact lenses comprising an aqueous solution comprising, before mixing, the following components:

(a) between about 10 and 400 ppm of a polyquaternium polymer comprising 10 to 45 mole percent of a quaternary-amine-functional repeat unit that is the copolymerization reaction product of one or more comonomers selected from the group consisting of substituted or unsubstituted vinylimidazoles or their vinylimidazoliuum salts, and mixtures thereof, which polymer has a weight average molecular weight of 5,000 to 5,000,000; and (b) a polymeric biguanide, in the total amount of between about 0.10 to about 3.0 ppm, having the formula:

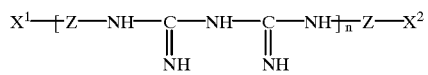

wherein Z is an organic divalent bridging group which may be the same or different throughout the polymer, n is on average at least 3, and $X^1$ and $X^2$ are independently selected from the groups

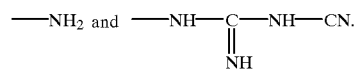

(c) an effective amount of a buffering agent to buffer said composition; and (d) water in an amount of at least 80% by weight.

2. The contact-lens solution of claim 1, wherein said polyquaternium polymer is present in an amount of between 50 and 300 ppm.

3. The contact-lens solution of claim 1, wherein said polyquaternium copolymer comprises 20 to 40 mole percent of said repeat unit.

4. The contact-lens solution of claim 1, wherein the polyquaternium copolymer is a copolymer of up to 90 mole percent of repeat units that are the reaction of one or more comonomer selected from the group consisting of vinylpyrrolidone, acrylamide, acrylic acid, methyl methacryate, and copolymerization-compatible mixtures thereof.

5. The contact-lens solution of claim 1, wherein the polymeric biguanide is a mixture of molecules with the general formula:

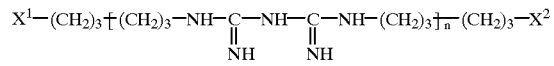

wherein $X^1$ and $X^2$ are as defined above and n is on average 5 to 20.

6. The contact-lens solution of claim 1, further comprising a neutral or non-ionic surfactant in the amount of 0.01 to 5.0 percent.

7. The contact-lens solution of claim 6, wherein the surfactant is a neutral or non-ionic surfactant having a plurality of poly(oxyalkylene) chains, each of the poly (oxyalkylene) comprises (—OR) repeat units, wherein R is independently an alkylene having 2 to 6 carbon atoms.

8. The contact-lens solution of claim 6, wherein the surfactant is a neutral or non-ionic surfactant which comprises a block copolymer of poly(ethyleneoxide) and poly (propylene oxide) segments.

9. The contact lens solution of claim 1, wherein the amount of biguanide polymer is 0.2 to 2.0 ppm.

10. The contact-lens solution of claim 9, wherein the amount of biguanide polymer is about 0.5 ppm to about 1.5 ppm.

11. The contact-lens solution of claim 1, wherein the buffering agent is a borate buffer system.

12. A method of treating a soft contact lens with a solution, which method comprises:

(a) soaking the lens in a solution, such that acceptable disinfection of the contact lens is obtained with the solution, the solution comprising, in formulation, the following components:

(i) a polyquaternium polymer, in the total amount of between about 10 and 400 ppm, which polyquaternium polymer comprises 10 to 45 mole percent of a quaternary-amine-functional repeat unit that is the copolymerization reaction product of one or more comonomers selected from the group consisting of substituted or unsubstituted vinylimidazoles or their vinylimidazoliuum salts and mixtures thereof, and which polymer has a weight average molecular weight of 5,000 to 5,000,000;

(ii) a polymeric biguanide, in the total amount of between about 0.10 to about 3.0 ppm, having the following general formula:

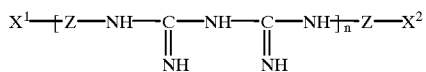

wherein Z is an organic divalent bridging group which may be the same or different throughout the polymer, n is on average at least 3, and $X^1$ and $X^2$ are independently selected from the groups

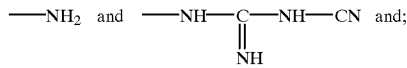

(iii) an effective amount of a buffering agent to buffer said composition; and (b) directly placing the treated lens on the eye of the wearer, wherein (i) rinsing with a different solution prior to replacement on the eye is not required, and (ii) no other solution is required for daily disinfection of the lens.

13. The method of claim 12 wherein the method of treated the contact lens does not include rubbing the lens with the solution, as not required by the instructions for use of the solution.

14. The method of claim 12, wherein the solution is a disinfecting solution.

15. The method of claim 12, wherein the solution is a multi-purpose solution or effective multipurpose solution.

16. The method of claim 12, wherein said polyquaternium polymer is present in an amount of between 50 and 300 ppm.

17. The method of claim 12, wherein said polyquaternium copolymer comprising 20 to 40 mole percent of said quaternary-amine-functional repeat unit.

18. The method of claim 12, wherein the polyquaternium copolymer is a copolymer of up to 90 mole percent of a repeat unit that is the reaction product of one or more comonomers selected from the group consisting of vinylpyrrolidone, acrylamide, acrylic acid, methyl methacryate, and copolymerization-compatible mixtures thereof.

19. The method of claim 12, wherein the polymeric biguanide is a mixture of polymeric biguanides having the following formula:

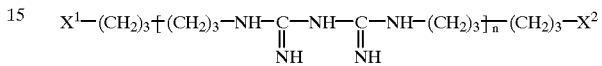

wherein $X^1$ and $X^2$ are as defined above and n is on average 5 to 20.

20. The method of claim 12, wherein the solution is used to treat a lens that is set or planned for replacement after not more than about 30 days of wear.

21. The method of claim 12, wherein the lens is planned or set for replacement after not more than about 14 days of wear.

22. The method of claim 12, wherein the solution is used to treat a lens that is made from a polymer comprising about 0.0 to 5 mole percent of repeat units derived from methacrylic acid (MAA), 10 to 99 mole percent of repeat units derived from hydroxyethyl methacrylate, and about 0.5 to 5 mole percent of cross-linking repeat units.

23. A kit for use by a contact-lens wearer for disinfecting or disinfecting and cleaning a contact lens, which kit comprising:

(a) a container with the ophthalmically safe disinfecting solution according to claim 1, and (b) instructions for use that comprise directions for the contact lens wearer to carry out the method according to claim 12.

* * * * *